(12) United States Patent
Lee et al.

(10) Patent No.: US 8,883,463 B2
(45) Date of Patent: Nov. 11, 2014

(54) RECOMBINANT MICROORGANISM HAVING ABILITY TO PRODUCE [LACTATE-CO-GLYCOLATE] COPOLYMER FROM GLUCOSE, AND METHOD FOR PREPARING [LACTATE-CO-GLYCOLATE] COPOLYMER USING SAME

(75) Inventors: Sang Yup Lee, Daejeon (KR); Si Jae Park, Daejeon (KR); Seung Hwan Lee, Daejeon (KR); Bong Keun Song, Daejeon (KR); Yu Kyung Jung, Daejeon (KR); Tae Woo Lee, Daejeon (KR)

(73) Assignees: Korea Advanced Institute of Science and Technology, Daejeon (KR); Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 14/004,437

(22) PCT Filed: Mar. 9, 2012

(86) PCT No.: PCT/KR2012/001754
§ 371 (c)(1),
(2), (4) Date: Oct. 18, 2013

(87) PCT Pub. No.: WO2012/124943
PCT Pub. Date: Sep. 20, 2012

(65) Prior Publication Data
US 2014/0030775 A1    Jan. 30, 2014

(30) Foreign Application Priority Data
Mar. 11, 2011    (KR) .................. 10-2011-0022020

(51) Int. Cl.
| | | |
|---|---|---|
| C12N 15/74 | (2006.01) | |
| C12N 5/04 | (2006.01) | |
| C12N 1/20 | (2006.01) | |
| C12P 7/62 | (2006.01) | |
| C12N 15/70 | (2006.01) | |
| C12N 9/04 | (2006.01) | |
| C12N 9/10 | (2006.01) | |

(52) U.S. Cl.
CPC ................ *C12P 7/625* (2013.01); *C12N 15/70* (2013.01); *C12N 9/0006* (2013.01); *C12N 9/1029* (2013.01)
USPC ......... 435/135; 435/419; 435/471; 435/252.3

(58) Field of Classification Search
USPC ................ 435/135, 252.3, 419, 471
See application file for complete search history.

(56) References Cited

U.S. PATENT DOCUMENTS

| | | |
|---|---|---|
| 6,143,952 A | 11/2000 | Srienc et al. |
| 2009/0155867 A1 | 6/2009 | Soucaille |
| 2010/0050298 A1 | 2/2010 | Park et al. |
| 2010/0136637 A1 | 6/2010 | Park et al. |
| 2011/0177569 A1 | 7/2011 | Park et al. |
| 2011/0201067 A1 | 8/2011 | Lee et al. |

FOREIGN PATENT DOCUMENTS

| | | |
|---|---|---|
| KR | 1020090017252 A | 2/2009 |
| KR | 1020090029256 A | 3/2009 |
| KR | 1020100002177 A | 1/2010 |
| KR | 100957777 B1 | 5/2010 |
| KR | 1020100111766 A | 10/2010 |
| KR | 102011006886 A | 6/2011 |
| WO | 9854329 A1 | 12/1998 |
| WO | 9961624 A2 | 12/1999 |
| WO | 0155436 A1 | 8/2001 |
| WO | 2011074842 A1 | 6/2011 |

OTHER PUBLICATIONS

Datsenko, K., et al., "One-step inactivation of chromosomal genes in *Escherichia coli* K-12 using PCR products", "Proc. Natl. Acad. Sci. USA", Jun. 6, 2000, pp. 6640-6645, vol. 97, No. 12.

Jacquel, N., et al., "Isolation and purification of bacterial poly(3-hydroxyalkonoates", "Biochemical Engineering Journal", 2008, pp. 15-27, vol. 39.

Langenbach, S., et al., "Functional expression of the PHA synthase gene phaC1 from *Pseudomonas aeruginosa* in *Escherichia coli* results in poly(3-hydroxyalkanoate) synthesis", "FEMS Microbiology Letter", 1997, pp. 303-309, vol. 150.

Qi, Q., et al., "Synthesis of poly(3-hydroxyalkanoates) in *Escherichia coli* expressing the PHA synthase gen phaC2 from *Pseudomonas aeruginosa*: comparison of PhaC1 and PhaC2","FEMS Microbiology Letters", 1997, pp. 155-162, vol. 157.

Qi, Q., et al., "Metabolic routing towards polyhydroxyalkanoic acid synthesis in recombinant *Escherichia coli* (fadR): inhibition of fatty acid B-oxidation by acrylic acid","FEMS Micorobiology Letters", 1998, pp. 89-94, vol. 167.

Rintala, E., et al., "The ORF YNL274c (GORI) codes for glyoxylate reductase in *Saccharomyces*", "Yeast", 2007, pp. 129-136, vol. 24.

Yang, T., et al., "Biosynthesis of Polylactic Acid and Its Copolymers Using Evolved Propionate CoA Transferace and PHA Synthase", "Biotechnology and Bioengeneering", Jan. 1, 2010, pp. 150-160, vol. 105, No. 1.

*Primary Examiner* — Maryam Monshipouri
(74) *Attorney, Agent, or Firm* — Hultquist, PLLC; Steven J. Hultquist

(57) ABSTRACT

There is provided a recombinant microorganism having producibility of poly(lactate-co-glycolate) from glucose, and more particularly, a recombinant microorganism having producibility of poly(lactate-co-glycolate) without adding an exogenous glycolate precursor, and a method of preparing [poly(preparing lactate-co-glycolate)] using the same. According to the present invention, the poly(lactate-co-glycolate) in which the concentration of the glycolate fraction is high may be prepared at a high concentration without supplying exogenous glyoxylate. Therefore, the present invention may be effectively used for treatment.

18 Claims, 4 Drawing Sheets

A)

B)

(A)

(B)

(C)

RECOMBINANT MICROORGANISM HAVING ABILITY TO PRODUCE [LACTATE-CO-GLYCOLATE] COPOLYMER FROM GLUCOSE, AND METHOD FOR PREPARING [LACTATE-CO-GLYCOLATE] COPOLYMER USING SAME

CROSS-REFERENCE TO RELATED APPLICATIONS

This application is a U.S. national phase under 35 U.S.C. §371 of International Patent Application No. PCT/KR12/01754 filed Mar. 9, 2012, which in turn claims priority of Korean Patent Application No. 10-2011-0022020 filed Mar. 11, 2011. The disclosures of such international patent application and Korean priority patent application are hereby incorporated herein by reference in their respective entireties, for all purposes.

TECHNICAL FIELD

The present invention relates to a recombinant microorganism having producibility of poly(lactate-co-glycolate) from glucose, and more particularly, to a recombinant microorganism having producibility of poly(lactate-co-glycolate) without adding an exogenous glycolate precursor, and a method of preparing poly(preparing lactate-co-glycolate) using the same.

BACKGROUND ART

Poly(lactate-co-glycolate) (PLGA), which is a representative biodegradable polymer derived from lactate and glycolate, is a polymer having high applicability to a general purpose polymer or medical polymer. Currently, the PLGA may be prepared by a direct polymerization reaction of lactate and glycolate, but PLGA having a low molecular weight (1000 to 5000 daltons) is mainly prepared in this reaction. PLGA having a high molecular weight of 100,000 daltons or more may be synthesized by a ring opening condensation reaction of lactide and glycolide. The lactide and glycolide, which are cyclic diesters of lactate and glycolate, respectively, are formed by pyrolysis of a lactate oligomer and a glycolate oligomer, respectively.

In the ring opening condensation reaction, a catalyst such as tin(II) 2-ethylhexanoate, tin(II) alkoxide, aluminum isopropoxide, or the like, should be used. As a method of preparing the PLGA having a high molecular weight, there is a method of polymerizing a polymer having a relatively high molecular weight from a polymer obtained by direct polymerization and having a low molecular weight using a chain coupling agent, but in this method, since the chain coupling agent is used, a process may be complicated due to addition of an organic solvent or the chain coupling agent, and it may be difficult to remove this organic solvent or chain coupling agent.

Currently, in a commercialized process for producing the PLGA having a high molecular weight, a method of converting lactate and glycolate into lactide and glycolide, respectively, and then synthesizing the PLGA through the ring opening condensation reaction of the lactide and glycolide has been used.

Meanwhile, poly(hydroxyalkanoate) (PHA) is a polyester accumulated by microorganism as an energy or carbon source storage material in the microorganism when the carbon source excessively exists but other nutrients such as phosphorus, nitrogen, magnesium, oxygen, and the like are insufficient. Since the PHA has complete biodegradability while having physical properties similar to those of the existing synthetic polymers derived from petroleum, the PHA has been recognized as a material replacing the existing synthetic plastic material.

The existing known PHA may be representatively divided into a short-chain-length PHA (SCL-PHA) having a short carbon chain and a medium-chain-length PHA (MCL-PHA) having a long carbon chain. Gene for synthesizing the PHA was cloned from *Ralstonia eutropha*, *Pseudomonas*, or the like, and PHA composed of various monomers was synthesized by recombinant microorganism (Qi et al., *FEMS Microbiol. Lett.*, 157:155, 1997; Qi et al., *FEMS Microbiol. Lett.*, 167:89, 1998; Langenbach et al., *FEMS Microbiol. Lett.*, 150:303, 1997; WO 01/55436; U.S. Pat. No. 6,143,952; WO 98/54329; WO 99/61624).

Since glycolic acid is the simplest hydrocarboxylic acid, there has been an attempt to insert glycolic acid into the PHA polymer using a PHA synthase enzyme of *Ralstonia europha* and a glycolyl-CoA produced from beta oxidation pathway as a substrate.

The present inventors confirmed that in the case of culturing recombinant *E. coli* transfected with propionate CoA-transferase gene (Pct) derived from *Clostridium propionicum*, which is gene coding an enzyme converting lactate and glycolate into lactyl-CoA and glycolyl-CoA, respectively, and poly(hydroxyalkanoate) (PHA) synthase gene using lactyl-CoA and glycolyl-CoA as substrates in a production medium containing glucose and glycolate or glucose, glycolate, and hydroxyalkanoate, poly(lactate-co-glycolate) and poly(lactate-co-glycolate-co-hydroxyalkanoate) were produced (Korean Patent Application No. 10-2009-0030133).

However, the method of producing PLGA using the recombinant *E. coli* has a disadvantage in that glucose and glycolate corresponding to precursors of the monomer should be individually added.

Therefore, the present inventors have tried to develop recombinant *E. coli* capable of producing PLGA in which a content of a glycolate fraction is high without adding exogenous glycolate, and confirmed that in the case of expressing glycerate dehydrogenase of *P. multocida* or *E. coli* in *E. coli* transfected with propionate CoA-transferase of *Clostridium propionicum* and PHA synthase of *Pseudomonas* sp. 6-19, deleting isocitrate lyase regulator gene (iclR) and aceB (malate synthase) gene, and amplifying isocitrate lyase gene (aceD), even though glycolate is not added, PLGA in which the content of the glycolate fraction is high may be produced at a high concentration using only glucose, thereby completing the present invention.

SUMMARY

An object of the present invention is to provide a recombinant microorganism capable of producing PLGA at a high concentration without adding exogenous glycolate.

Another object of the present invention is to provide a method of preparing PLGA using a recombinant microorganism capable of producing PLGA at a high concentration without adding exogenous glycolate.

According to an aspect of the present invention, there is provided a mutant transfected with a gene coding poly(hydroxyalkanoate) (PHA) synthase, a gene coding propionyl-CoA transferase, and a gene coding glycerate dehydrogenase (EC 1.1.1.26).

According to another aspect of the present invention, there is provided a mutant transfected so that a gene coding PHA synthase, a gene coding propionyl-CoA transferase, and a gene coding glycerate dehydrogenase (EC 1.1.1.26) are inserted, a gene (iclR) coding isocitrate lyase regulator or a aceB (malate synthase) gene is deleted.

According to another aspect of the present invention, there is provided a method of preparing poly(lactate-co-glycolate) (PLGA) including: culturing a mutant transfected with a gene coding poly(hydroxyalkanoate) (PHA) synthase, a gene coding propionyl-CoA transferase, and a gene coding glycerate dehydrogenase (EC 1.1.1.26) in a glucose-containing medium to produce PLGA; and obtaining the produced PLGA.

According to another aspect of the present invention, there is provided a method of preparing poly(lactate-co-glycolate) (PLGA) including: culturing a mutant transfected so that a gene coding PHA synthase, a gene coding propionyl-CoA transferase, and a gene coding glycerate dehydrogenase (EC 1.1.1.26) are inserted, a gene (iclR) coding isocitrate lyase regulator or aceB (malate synthase) gene is deleted, and a gene (aceA) coding isocitrate lyase is amplified in a glucose-containing medium to produce PLGA; and obtaining the produced PLGA.

Other features and embodiments of the present invention will become obvious from the following detailed description and the accompanying claims.

DETAILED DESCRIPTION OF THE EMBODIMENTS

Figure 1:
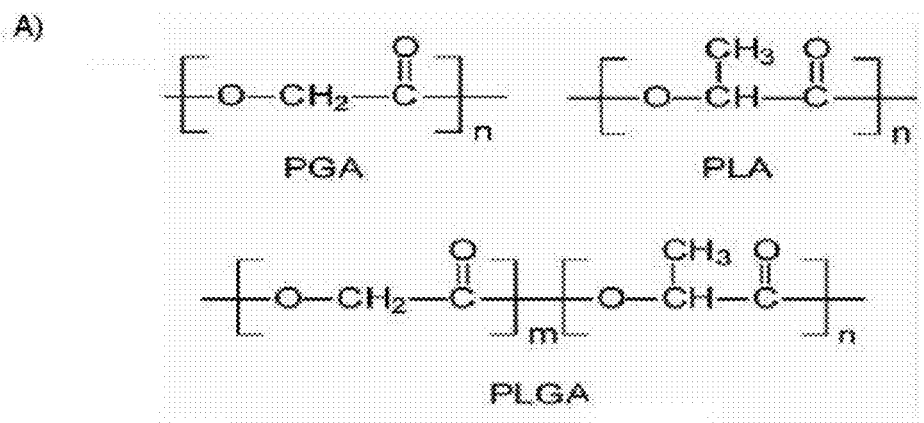
FIG. 1A shows Chemical Formulas of poly(lactate-co-glycolate) (PLGA), poly-gamma-glutamic acid (PGA), and polylactic acid (PLA) prepared in the present invention.
FIG. 1B shows a PLGA production pathway by metabolic engineering performed in the present invention.
Figure 1:
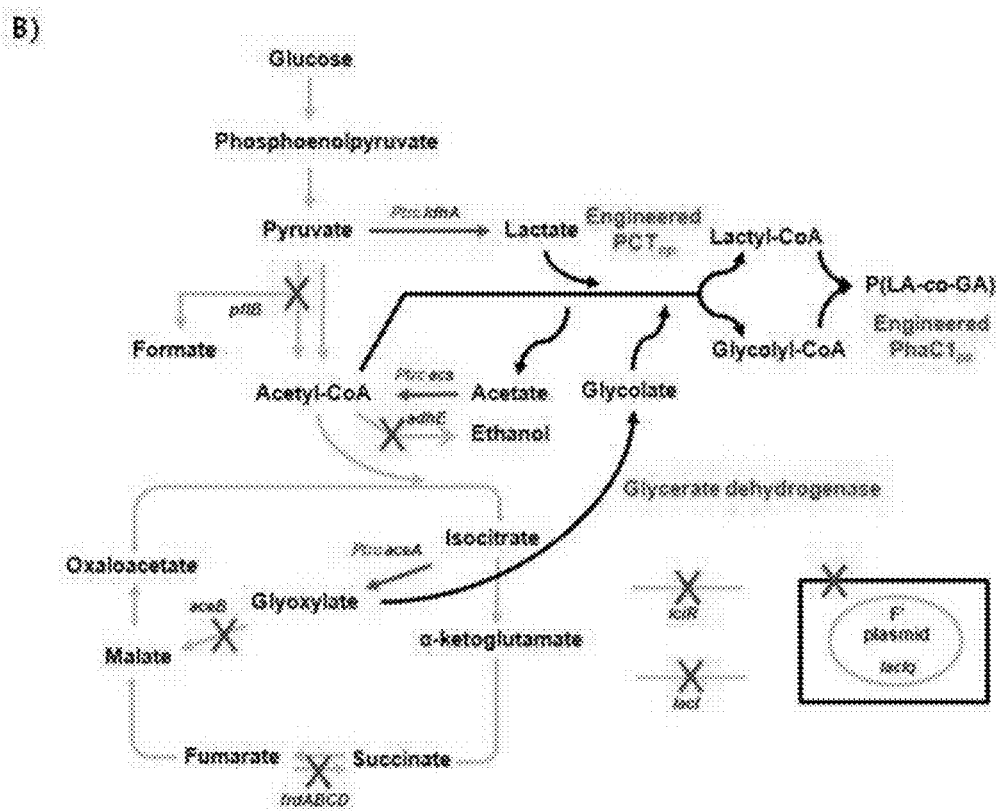
Figure 2:
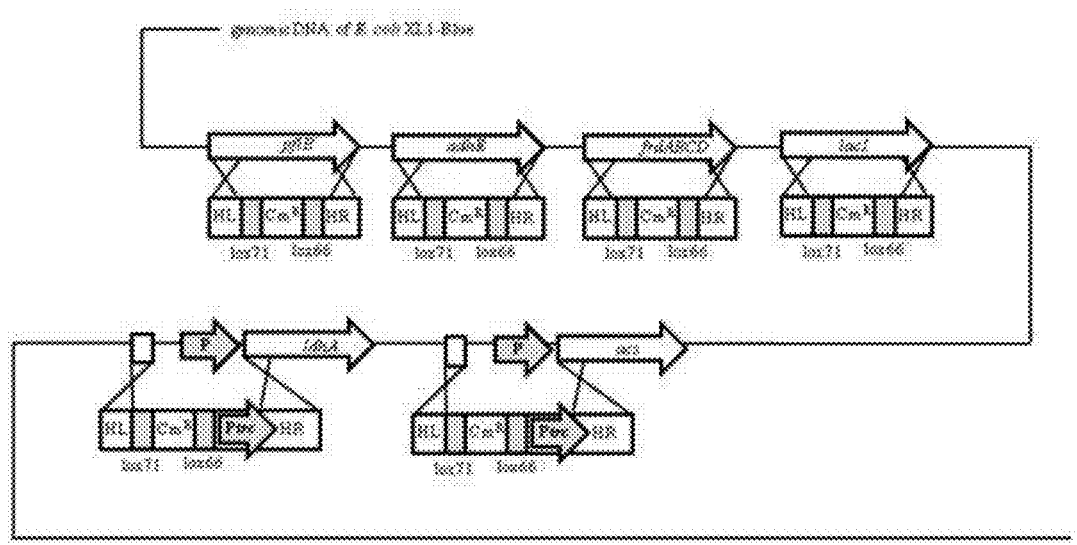
FIG. 2 shows a map of genes associated with production of PLGA in chromosome of E. coli XL1-Blue.
Figure 3:
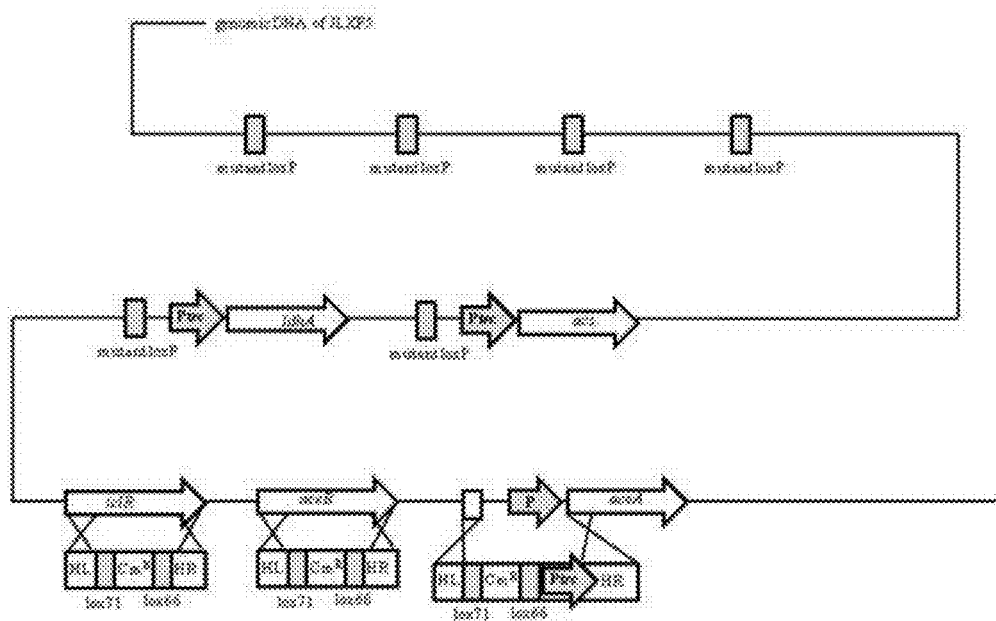
FIG. 3 shows a map of genes associated with production of PLGA in chromosome of recombinant E. coli JLXF5 constructed in the present invention.
Figure 4:
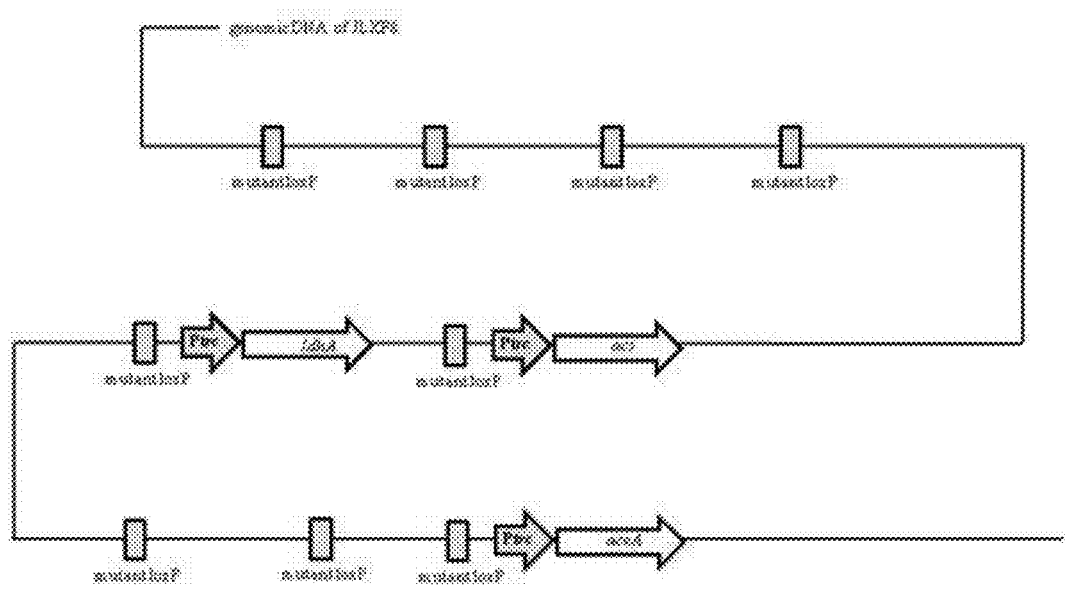
FIG. 4 shows a map of genes associated with production of PLGA in chromosome of recombinant E. coli JLXF8 constructed in the present invention.

Unless otherwise defined herein, technical and scientific terms used in the present specification have the same meanings as those understood by specialists in the skilled art to which the present invention pertains. Generally, nomenclature used in the present specification is well known and commonly used in the art.

In one general aspect, the present invention relates to a recombinant microorganism transfected with a gene coding poly(hydroxyalkanoate) (PHA) synthase, a gene coding propionyl-CoA transferase, and a gene coding glycerate dehydrogenase (EC 1.1.1.26) and having producibility of poly (lactate-co-glycolate).

The propionate CoA-transferase may be propionate CoA-transferase of C. propionicum or Pct540, which is a mutant enzyme of propionate CoA-transferase of C. propionicum, and poly(hydroxyalkanoate) (PHA) synthase may be PHA synthase of Pseudomonas sp. 6-19 or a mutant enzyme of PHA synthase of Pseudomonas sp. 6-19.

The gene coding the mutant enzyme of the PHA synthase may have a base sequence corresponding to an amino acid sequence including at least one mutation selected from a group consisting of E130D, S325T, L412M, S477R, S477H, S477F, S477Y, S477G, Q481M, Q481K, and Q481R in an amino acid sequence of SEQ ID No: 1. In addition, the gene coding the mutant enzyme of the PHA synthase may have a base sequence corresponding to an amino acid sequence selected from a group consisting of an amino acid sequence C1335 in which E130D, S325T, L412M, S477G, and Q481M in the amino acid sequence of SEQ ID No: 1 are mutated; an amino acid sequence C1310 in which E130D, S477F, and Q481K in the amino acid sequence of SEQ ID No: 1 are mutated; and an amino acid sequence C1312 in which E130D, S477F, and Q481R in the amino acid sequence of SEQ ID No: 1 are mutated.

The gene coding glycerate dehydrogenase (EC 1.1.1.26) may be derived from Pasteurella multocida or E. coli and have a base sequence of SEQ ID No: 2.

In another aspect, the present invention relates to a recombinant microorganism transfected so that a gene coding PHA synthase, a gene coding propionyl-CoA transferase, and a gene coding glycerate dehydrogenase (EC 1.1.1.26) are inserted, a gene (iclR) coding isocitrate lyase regulator or aceB (malate synthase) gene is deleted, and a gene (aceA) coding isocitrate lyase is amplified, and having producibility of poly(lactate-co-glycolate).

In the present invention, the term "deletion" means that genes are modulated so as to allow a protein coded by the gene not to perform its original function through substitution, removal, and mutation.

In the present invention, both of the gene (iclR) coding isocitrate lyase regulator and aceB (malate synthase) genes may be deleted.

In the present invention, in the recombinant microorganism, the gene (aceA) coding isocitrate lyase may be additionally amplified.

In the present invention, a parent strain of the mutant may be selected from a group consisting of E. coli XL1-Blue, E. coli JLX5, E. coli JLX6, E. coli JLX7, E. coli JLX8, E. coli JLX10, E. coli JLX11, E. coli JLX12, and E. coli JLX13, and features of the parent strain were shown in Table 1.

In another aspect, the present invention relates to a method of preparing poly(lactate-co-glycolate) (PLGA) including: culturing a recombinant microorganism transfected with a gene coding poly(hydroxyalkanoate) (PHA) synthase, a gene coding propionyl-CoA transferase, and a gene coding glycerate dehydrogenase (EC 1.1.1.26) in a glucose-containing medium to produce PLGA; and obtaining the produced PLGA.

In the present invention, an E. coli strain producing the PLGA, which is a polymer that is not produced in a natural state, was developed, and a production amount of glycolate, which is a monomer of the PLGA, may be further increased by modulating a metabolic pathway of E. coli.

In one aspect, a recombinant E. coli JLXF5 strain expressing Pct540$_{Cp}$, PhaC1437$_{Ps6-19}$, and glycerate dehydrogenase of P. multocida produces 33.6 weight % of P(35.2 mol % LA-co-64.8 mol % GA). This result is a first study in which the poly(lactate-co-glycolate) is produced from glucose in metabolically engineered recombinant E. coli.

In another aspect, the present invention relates to a method of preparing poly(lactate-co-glycolate) (PLGA) including: culturing a recombinant microorganism in which a gene coding PHA synthase, a gene coding propionyl-CoA transferase, and a gene coding glycerate dehydrogenase (EC 1.1.1.26) are inserted, a gene (iclR) coding isocitrate lyase regulator or aceB (malate synthase) gene is deleted in a glucose-containing medium to produce PLGA; and obtaining the produced PLGA.

EXAMPLE

Hereinafter, the present invention will be described in detail through the Examples. However, these Examples are only to illustrate the present invention, and those skilled in the art will appreciate that these Examples are not to be construed as limiting a scope of the present invention.

Example 1

Used Strain and Analysis Method

Strains, plasmids, and primers used in the following Examples were shown in Table 1.

In the following Example, a MR medium used to produce a PLGA in a recombinant *E. coli* may contain 6.67 g of $KH_2PO_4$, 4 g of $(NH_4)_2HPO_4$, 0.8 g of $MgSO_4H_2O$, 0.8 g of citric acid, and 5 ml of a trace metal solution per 1 L, wherein the trace metal solution contains 0.5M HCl: 10 g of $FeSO_4.H_2O$, 2 g of $CaCl_2$, 2.2 g of $ZnSO_4.H_2O$, 0.5 g of $MnSO_4.H_2O$, 1 g of $CuSO_4.H_2O$, 0.1 g of $(NH_4)_6Mo_7O_{24}.H_2O$, and 0.02 of $Na_2B_4O_7.10H_2O$, Carbon source, and $MgSO_4.H_2O$ per 1 L.

In culturing each strain, a seed strain was shaking-cultured in a 25 mL tube in which 10 mL of LB medium was added at 30° C. overnight, and 1 mL of the cultured solution was inoculated into a 250 mL flask charged with 100 mL of the MR medium containing glucose (20 g/L) and shaking-cultured at 30° C. for 72 hours. In the case of synthesizing p(3HB-co-LA-co-GA), 3HB (2 g/L) was added to a culture medium.

In the case of using JLX10 strains (Jung et al., 2010) as a host cell, in order to overcome growth restriction caused by ppc gene deletion, 4 g/L of sodium succinate (Sigma-Aldrich, USA) was added to the culture medium, and in order to express ldhA and acs genes regulated by a trc promoter, when an $OD_{600}$ value was 0.5, 1 mM IPTG was added. As needed, ampicillin (100 μM/mL), chloramphenicol (34 μg/mL), and thiamine (10 μg/mL) were added to the medium.

Genetic characteristics of the recombinant strains and plasmids used in the present invention were shown in Table 1, and the primers used to construct the recombinant strains and plasmids in the present invention were shown in Table 2.

In constructing the recombinant strain used in the present invention, as a method of deleting iclR and aceB genes in chromosome and replacing a promoter of aceA gene with a trc promoter, a one-step inactivation method using the primer shown in Table 2 was used (Datsenko and Wanner, Proc. Natl. Acad. Sci. USA. 6; 97:6640, 2000).

TABLE 1

| Strain, Plasmid or Primer | characteristic[a] | Reference or receving area |
|---|---|---|
| Strain | | |
| XL1-Blue | recA1 endA1 gyrA96 thi-1 hsdR17 supE44 relA1 lac [F' proAB lacI<sup>q</sup>ZΔM15 Tn10 (Tet<sup>R</sup>)] | Stratagene[b] |
| JLX10 | XL1-Blue ΔackA PldhA::Ptrc Δppc Pacs::Ptrc ΔadhE | Present invention |
| JLX11 | JLX10 ΔiclR | Present invention |
| JLX12 | JLX10 ΔaceB PaceA::Ptrc | Present invention |
| JLX13 | JLX10 ΔiclR ΔaceB PaceA::Ptrc | Present invention |
| JLXF5 | XB-F ΔiacI ΔpflB ΔfrdABCD ΔadhE PldhA::Ptrc Pacs::Ptrc | Present invention |
| JLXF6 | JLXF5 ΔiclR | Present invention |
| JLXF7 | JLXF5 ΔaceB PaceA::Ptrc | Present invention |
| JLXF8 | JLXF5 ΔiclR ΔaceB PaceA::Ptrc | Present invention |
| | | Present invention |
| Plasmid | | |
| pBluescript | Ap<sup>R</sup>, cloning and expression vector | Stratagene[b] |
| pPs619C1400-CpPCT532 | Ap<sup>R</sup>, Promoter of the *C. necator* PHA biosynthesis operon, phaC1<sub>Ps6-19</sub> variant (phaC1400<sub>Ps6-19</sub>; E130D, S325T, S477R, Q481M), pct<sub>Cp</sub> variant (pct532<sub>Cp</sub>; A243T, silent mutations: A1200G), transcriptional terminator of the *C. necator* PHA biosynthesis operon, derivative of pBluescript II KS(+) | Present invention |
| pPs619C1310-CpPCT540 | AP<sup>R</sup>, Promoter of the *C. necator* PHA biosynthesis operon, phaC1<sub>Ps6-19</sub> variant (phaC1310<sub>Ps6-19</sub>; E130D, S477F, Q481K), pct<sub>Cp</sub> variant (pct540<sub>Cp</sub>; | Korean Patent Laid-Open Publication No. 2010-0111766 |

TABLE 1-continued

| Strain, Plasmid or Primer | characteristic[a] | Reference or receding area |
|---|---|---|
| | V193A, Silent mutations: T78C, T669C, A1125G, T1158C), transcriptional terminator of the *C. necator* PHA biosynthesis operon, derivative of pBluescriptII KS(+) | |
| pPs619C1437-CpPCT540 | AP[R], Promoter of the *C. necator* PHA biosynthesis operon, phaC1$_{Ps6-19}$ variant (phaC1337$_{Ps6-19}$; E130D, S325T, S477G, Q481K), pct$_{Cp}$ variant (pct540$_{Cp}$; V193A, Silent mutations: T78C, T669C, A1125G, T1158C), transcriptional terminator of the *C. necator* PHA biosynthesis operon, derivative of pBluescriptll KS(+) | Present invention |
| pTac15k | p15A origin of replication, Km[R], tac promoter | Lab stock |
| pTac15kPmu0559 | Derivative of pTac15k, expression of *Pasteurella multocida* glycerate dehydrogenase gene under tac promoter | Present invention |
| pBBR1MCS2 | Broad host range vector; Km[r] | |
| pZE12-MCS | Expression vector; $P_{LlacO-1}$ promoter; Ap[r] | EXPRESSYS[c] |
| pKE12-MCS | Expression vector; $P_{LlacO-1}$ promoter, *R. eutropha* PHA biosynthesis genes transcription terminator; Ap[r] | Present invention |
| pZA31-MCS | Expression vector; $P_{LtetO-1}$ promoter; Cm[r] | EXPRESSYS |
| pKA32-MCS | Expression vector; $P_{LlacO-1}$ promoter, *R. eutropha* PHA biosynthesis genes transcription terminator; Cm[r] | Present invention |
| pKM22-MCS | Expression vector; $P_{LlacO-1}$ promoter; Km[r] | Present invention |
| pKM22-YcdW | Derivative of pKM22-MCS, expression of *E. coli* glycerate dehydrogenase gene (ycdW) under lacIO promoter | Present invention |
| Primer | | |
| PmuFEcoRI (SEQ ID NO: 3) | GTAGAATTCATGTTAAAAATTGTTTTTCTAGATAGTACC | Present invention |
| PmuRPstI (SEQ ID NO: 4) | GTATGCAACTGCAGTTAAGCAATCTGCTCATTTTTTAC | Present invention |

[a]Ap: ampicillin; Km: kanamycin; R: resistance.
[b]Stratagene Cloning System, La Jolla, CA, USA.
[c]www.expressys.com

TABLE 2

Primer list

JLX10 K.O.

| adhE | FDadhE1 (SEQ ID NO: 5) | TCGAGCAGATGATTTACTAAAAAAGTTTAACATTATCAGGAGAGCATTATTAGGTGACACTATAGAACGCG |
|---|---|---|
| | RdadhE1 (SEQ ID NO: 6) | GATTTTCATAGGTTAAGCAAATCATCACCGCACTGACTATACTCTCGTATTCGAGCAGATGATTTACTAA |
| | FDadhE2 (SEQ ID NO: 7) | TGATCGGCATTGCCCAGAAGGGGCCGTTTATGTTGCCAGACAGCGCTACTTAGTGGATCTGATGGGTACC |

TABLE 2-continued

Primer list

|  |  |  |
|---|---|---|
|  | RdadhE2<br>(SEQ ID NO: 8) | GGAAGCCGTTATAGTGCCTCAGTTTAAGGATCGGTCAACTAATCCTTA<br>ACTGATCGGCATTGCCCAGAAG |
| Ptrc |  |  |
| acs | FPacs1<br>(SEQ ID NO: 9) | TCACGACAGTAACCGCACCTACACTGTCATGACATTGCTCGCCCCTA<br>TGTGTAACAAATA |
|  | RPacs1<br>(SEQ ID NO: 10) | TGTTATCCGCTCACAATTCCACACATTATACGAGCCGGATGATTAAT<br>TGTCAACAGCTAGTGGATCTGATGGGTACC |
|  | FPacs2<br>(SEQ ID NO: 11) | TCACGACAGTAACCGCACCTACACTGTCATGACATTGCTCGCCCCTA<br>TGTGTAACAAATA |
|  | RPacs2<br>(SEQ ID NO: 12) | CGATGTTGGCAGGAATGGTGTGTTTGTGAATTTGGCTCATGGTCTGT<br>TTCCTGTGTGAAATTGTTATCCGCTCACAATTCC |
|  | FPacs3<br>(SEQ ID NO: 13) | CGAATTGCGCCATTGTTGCAATGGCGGTTTTTATTGTTTTTCACGAC<br>AGTAACCGCACCT |
|  | RPacs3<br>(SEQ ID NO: 14) | TTGTTGATACATCGCCTCGTACTGCTGAGGGTTTATCAGGCAACGGT<br>CTGCGATGTTGGCAGGAATGGTG |
| JLXF5<br>K.O. |  |  |
| pflB | FDpflB1<br>(SEQ ID NO: 15) | TTACGGGCCTATAAGCCAGGCGAGATATGATCTATATCAATTTCTCA<br>TCTTAGGTGACACTATAGAACGCG |
|  | RDpflB1<br>(SEQ ID NO: 16) | TTCTTTAGTCAGCGAGTTGAAACGTACTGCGTAGCCAGATACACGGA<br>TGGTAGTGGATCTGATGGGTACC |
|  | FDpflB2<br>(SEQ ID NO: 17) | TATTTGGATAATCAAATATTTACTCCGTATTTGCATAAAAACCATGC<br>GAGTTACGGGCCTATAAGCCAGG |
|  | RDpflB2<br>(SEQ ID NO: 18) | TCTAATTACATAGATTGAGTGAAGGTACGAGTAATAACGTCCTGCTG<br>CTGTTCTTTAGTCAGCGAGTTGA |
| frdA<br>BCD | FDfrd1<br>(SEQ ID NO: 19) | ATTACGTGCTGCAATTGCTGCCGCGCAGGCAAATCCGAATGCAAAAA<br>TCGTAGGTGACACTATAGAACGCG |
|  | RDfrd1<br>(SEQ ID NO: 20) | GACCGTAGAAAACCCATTTGCCCGCAGGTACGTGGATTTTCAGATCG<br>TGCTAGTGGATCTGATGGGTACC |
|  | FDfrd2<br>(SEQ ID NO: 21) | GTGCAAACCTTTCAAGCCGATCTTGCCATTGTAGGCGCCGGTGGCGC<br>GGGATTACGTGCTGCAATTGCTG |
|  | RDfrd2<br>(SEQ ID NO: 22) | TTAGATTGTAACGACACCAATCAGCGTGACAACTGTCAGGATAGCAG<br>CCAGACCGTAGAAAACCCATTTG |
| adhE | FDadhE1<br>(SEQ ID NO: 23) | TCGAGCAGATGATTTACTAAAAAAGTTTAACATTATCAGGAGAGCAT<br>TATTAGGTGACACTATAGAACGCG |
|  | RDadhE1<br>(SEQ ID NO: 24) | TGATCGGCATTGCCCAGAAGGGGCCGTTTATGTTGCCAGACAGCGCT<br>ACTTAGTGGATCTGATGGGTACC |
|  | FDadhE2<br>(SEQ ID NO: 25) | GATTTTCATAGGTTAAGCAAATCATCACCGCACTGACTATACTCTCG<br>TATTCGAGCAGATGATTTACTAA |
|  | RDadhE2<br>(SEQ ID NO: 26) | GGAAGCCGTTATAGTGCCTCAGTTTAAGGATCGGTCAACTAATCCTT<br>AACTGATCGGCATTGCCCAGAAG |
| lacI | FDlacI1<br>(SEQ ID NO: 27) | TCAGACCGTTTCCCGCGTGGTGAACCAGGCCAGCCACGTTTCTGCGA<br>AAATAGGTGACACTATAGAACGCG |
|  | RDlacI1<br>(SEQ ID NO: 28) | TGCCAGCTGCATTAATGAATCGGCCAACGCGCGGGGAGAGGCGGTTT<br>GCGTAGTGGATCTGATGGGTACC |
|  | FDlacI2<br>(SEQ ID NO: 29) | GTGAAACCAGTAACGTTATACGATGTCGCAGAGTATGCCGGTGTCTC<br>TTATCAGACCGTTTCCCGCGTGG |
|  | RDlacI2<br>(SEQ ID NO: 30) | CATTAATTGCGTTGCGCTCACTGCCCGCTTTCCAGTCGGGAAACCTG<br>TCGTGCCAGCTGCATTAATGAAT |

TABLE 2-continued

Primer list

Ptrc

| | | |
|---|---|---|
| ldhA | FPldhA1<br>(SEQ ID NO: 31) | CATCTAATGCAATACGTGTCCCGAGCGGTAGCCAGATGCTAGGTGAC<br>ACTATAGAACGCG |
| | RPldhA1<br>(SEQ ID NO: 32) | TGTTATCCGCTCACAATTCCACACATTATACGAGCCGGATGATTAAT<br>TGTCAACAGCTAGTGGATCTGATGGGTACC |
| | FPldhA2<br>(SEQ ID NO: 33) | GATCGGGAATGATTAAACCTTTACGCGTAATGCGTGGGCTTTCATCT<br>AATGCAATACGTGTC |
| | RPldhA2<br>(SEQ ID NO: 34) | TCTTGTCGTACTGTTTTGTGCTATAAACGGCGAGTTTCATGGTCTGT<br>TTCCTGTGTGAAATTGTTATCCGCTCACAATTCC |
| | FPldhA3<br>(SEQ ID NO: 35) | GGTGATATGCGCAAGCTGACAATCTCCCACCAGATAACGGAGATCGG<br>GAATGATTAAACC |
| | RPldhA3<br>(SEQ ID NO: 36) | CAAAAAATTCCAGCTCAAAGCCAAAGGACTCGTTCACCTGTTGCAGG<br>TACTTCTTGTCGTACTGTTTTGTG |
| acs | FPacs1<br>(SEQ ID NO: 37) | TCACGACAGTAACCGCACCTACACTGTCATGACATTGCTCGCCCCTA<br>TGTGTAACAAATA |
| | RPacs1<br>(SEQ ID NO: 38) | TGTTATCCGCTCACAATTCCACACATTATACGAGCCGGATGATTAAT<br>TGTCAACAGCTAGTGGATCTGATGGGTACC |
| | FPacs2<br>(SEQ ID NO: 39) | TCACGACAGTAACCGCACCTACACTGTCATGACATTGCTCGCCCCTA<br>TGTGTAACAAATA |
| | RPacs2<br>(SEQ ID NO: 40) | CGATGTTGGCAGGAATGGTGTGTTTGTGAATTTGGCTCATGGTCTGT<br>TTCCTGTGTGAAATTGTTATC CGCTCACAATTCC |
| | FPacs3<br>(SEQ ID NO: 41) | CGAATTGCGCCATTGTTGCAATGGCGGTTTTTATTGTTTTTCACGAC<br>AGTAACCGCACCT |
| | RPacs3<br>(SEQ ID NO: 42) | TTGTTGATACATCGCCTCGTACTGCTGAGGGTTTATCAGGCAACGGT<br>CTGCGATGTTGGCAGGAATGGTG |

PLGA K.O.

| | | |
|---|---|---|
| iclr | 11HLiclR-inXB:<br>(SEQ ID NO: 43) | TGAAAATGATTTCCACGATACAGAAAAAAGAGACTGTCATGGTCGCA<br>CCCATTCCGCATCAGAGCAGATTGTACTGAGAG |
| | 12HLiclR-inXB:<br>(SEQ ID NO: 44) | TGATGGGCAGAATATTGCCTCTGCCCGCCAGAAAAAGTCAGCGCATT<br>CCACCGTACCTGATTCTGTGGATAACCGTATTAC |

K.O. + PaceA

| | | |
|---|---|---|
| aceB-A | 11HLaceB-A_PC inXB:<br>(SEQ ID NO: 45) | GCGGATAAATCGCTGGAAGCCAATAACGGTCACGATGGCACATGGAT<br>CGCCGCGTCATACACATACGATT |
| | 12HRaceB-A PC-inXB:<br>(SEQ ID NO: 46) | GGTTGAGTCCACTCTTTCTGTAATTCTTCAATTTGTTGTGTACGGGT<br>TTTCATGGTCTGTTTCCTGTGTG |
| ycdWF | ycdWf-EcoRI<br>(SEQ ID NO: 47) | gaattc atggatatcatcttttatcac |
| | ycdWb-KpnI<br>(SEQ ID NO: 48) | ggtacc ttagtagccgcgtgcgcggtc |
| hprAf | hprAf-EcoRI<br>(SEQ ID NO: 49) | gaattc atgcccagcccgcgtcgcgc |
| | hprAb-KpnI<br>(SEQ ID NO: 50) | ggtacc tcagctgaccacgcggcgtg |

Cell Growth and Metabolite Analysis

Metabolites including glucose, pyruvic acid, acetic acid, formic acid, lactate, and succinate were analyzed by HPLC (Varian ProStar 210, USA) equipped with UV/VIS (Varian ProStar 320, USA) and refractive index (Shodex RI-71, Japan) using a MetaCarb 87H column (300×7.8 mM). Cell growth was measured at 600 nm absorbance using Ultraspec 300 spectrophotometer (Amersham Bioscience, Sweden).

Example 2

Biosynthesis of P(LA-co-GA) Using *E. coli* Expressing PHA Synthase, Propionyl-CoA Transferase, and Glycerate Dehydrogenase In the present Example, in order to construct a recombinant *E. coli* producing P(LA-co-GA) in which a glycolate fraction is increased, genes to be inserted were selected.

It was confirmed through previous study (Korean Patent Laid-Open Publication No. 2010-0111766) that *E. coli* transfected with enzyme (Pct 540) having V193A mutation and 4 silent mutations of T78C, T669C, A1125G, and T1158C in the propionate CoA-transferase of *Clostridium propionicum* and enzyme having quadruple mutation PhaC1437 (E130D, S325T, S477G, and Q481K) in the PHA synthase of *Pseudomonas* sp. 6-19 may produce the P(LA-co-GA) having a high lactate fraction, and in order to synthesize the P(LA-co-GA), two mutated enzymes were selected.

First, in order to prepare a polymer containing glycolate, sodium glycolate was added to the medium at a concentration of 2 g/L as a precursor of glycolyl-CoA. It was reported that glycolate was used as a single carbon source in *E. coli*, but the concentration of the glycolate in the medium was not decreased during a culture period. When 3HB and glycolate were added to the medium at a concentration of 2 g/L, respectively, glycolate was not used to synthesize P(3HB-co-LA). This result means that a glycolate transport system mediated by glycolate permease (GlcA) did not operate under the present experimental condition.

Therefore, in order to overcome the problem that glycolate was not transported into the cells, the present inventors allowed glycolate to be produced from glyoxylate by glyoxylate reductase/glycerate dehydrogenase (FIG. 1B)

A reaction of converting glycerate into glycolate was performed by enzyme commission (EC) Nos. 1.1.1.79 (NAD(P) H-dependent glyoxylate reductase), 1.1.1.29 (NADH-dependent glyoxylate reductase), or 1.1.1.26 (glycerate dehydrogenase). Productivity of glycolate for synthesizing the PLGA copolymer from glucose was confirmed using NADPH-dependent glyoxylate reductase (EC 1.1.1.79) genes of *E. coli* MG1655 purchased from ATCC and KCTC and *E. coli* MG1655 strains amplified from chromosome of *P. putida* KT2440 and *P. multocida* and glycerate dehydrogenase (EC 1.1.1.26) genes of *P. putida* KT2440 and *P. multocida*.

As a result, among these genes, only glycerate hydrogenase (SEQ ID No: 51) of *E. coli* and glycerate hydrogenase (SEQ ID No: 2) of *P. multocida* may produce the PLGA copolymer, but in the case of using the glycerate hydrogenase of *P. multocida*, since the GA fraction in the polymer was higher than in the case of using the glycerate hydrogenase of *E. coli*, the glycerate hydrogenase of *P. multocida* was used in the following Experiments.

TABLE 3

| recombinant strain | polymer | Polymer composition (mol %) | | Polymer concentration (wt %) |
|---|---|---|---|---|
| | | LA | GA | |
| XB/pPs619C1437-CpPCT540 + pTac15kPmu0559[1] | P(LA-co-GA) | 47.8 | 52.2 | 12.3 |
| XB/p619C1437-PCT540 + pKM22-ycdW | P(LA-co-GA) | 61.4 | 38.6 | 12.8 |

Recombinant *E. coli* XL-1 Blue strains expressing Pct540$_{Cp}$, PhaC1437$_{Ps6\text{-}19}$, and the glycerate dehydrogenase of *P. multocida* produced P(47.8 mol % LA-co-52.2 mol % GA) at a polymer concentration of 12.3 weight % (Table 3).

The PHA synthase of *Pseudomonas* sp. 6-19 did not efficiently produce a polymer containing lactate without 3HB, which is a monomer having the highest affinity in synthesis of the polymer, which may be caused by low substrate-specificity to lactyl-CoA and a restricted content of lactyl-CoA in wild-type *E. coli* strain. It was thought that 3HB-CoA maybe serves as an initiator in synthesizing the polymer containing lactate (Yang et al., *Biotechnol. Bioeng.*, 105; 150, 2010). However, at the time of synthesizing PLGA, even in the case of not adding 3HB, the lactate monomer was efficiently contained in the PLGA at 50 mol % or more, such that it was confirmed that the glycolyl-CoA was a substrate having significant affinity for PhaC1437$_{Ps6\text{-}19}$ and may be used as an initiator such as 3HB. The glycolyl-CoA was produced by the recombinant *E. coli* expressing glycerate dehydrogenase of *P. multocida* shown in Table 2.

As a result, it may be appreciated that an enzyme activity of glycerate dehydrogenase of *P. multocida* plays an important role in synthesizing glycolate from glycerate.

In measuring the enzyme activity, after 10 hours and 70 hours of 1 mM isopropylthiogalactoside (IPTG) induction, the recombinant *E. coli* was sampled and centrifuged at 10,000×g for 5 minutes to obtain a cell pellet. Then, the obtained cell pellet was washed with a TDM buffer (50 mM Tris hydrochloride, 10 mM MgCl2, and 1 mM dithiothreitol, pH 7.5) two times, and suspended in the same buffer, followed by destructing cells using a titanium probe 40T (diameter: 4 mm, length: 127 mm) of an ultrasonic homogenizer (VCX-600, Sonics and Materials Inc., USA). Then the resultant was centrifuged at 4° C. and 16,000×g for 10 minutes, and the supernatant was used to measure the enzyme activity. A protein concentration of the cell extracts for measuring the enzyme activity was measured by a Bradford method.

In this case, the enzyme activity was an average value obtained by repeating the measuring experiment 3 times, and the recombinant JLX10 strain was cultured at 30° C. or 72 hours using a MR medium to which 20 g/L glucose and 4 g/L succinate were added. The recombinant XL1-Blue strain was cultured in a MR medium to which only 20 g/L glucose was added.

The sample for analyzing the enzyme activity was extracted after 10 hours and 70 hours of 1 mM isopropylthiogalactoside (IPTG) induction. 1 unit of enzyme activity was defined as the amount of enzyme converting a 1 mmole of a substrate into a specific product at 30° C. for 1 minute. A unit of activity was defined as unit/mg protein.

The enzyme activity was analyzed at 30° C. using a temperature control spectrophotometer (SpectraMax M2, Molecular Devices Co., USA). The enzyme activity was repeatedly tested 3 times and analyzed, and an amount of cell extract solution used in analysis was 16.5 μL/mL. Analysis of the reaction was performed by monitoring NAD(P)H at 340 nm, a value used as an extinction coefficient of NAD(P)H at 340 nm was 6.23/mM/cm, and 1 unit of enzyme activity was defined as the amount of enzyme converting a 1 mmole of a substrate into a specific product at 30° C. for 1 minute. A unit of activity was defined as unit/mg protein.

The activity of the glycerate dehydrogenase of *P. multocida* was analyzed by a method suggested by Rintalls et al, (Rintalla et al., Yeast, 24, 129-136, 2007). A reaction was carried out by adding glyoxylate to the reaction mixture containing 50 mM sodium phosphate buffer (pH 7.0), the cell extracts, and 0.2 mM NAD(P)H so that a concentration of glyoxylate became 25 mM, and the reaction mixture to which glyoxylate was not added was used as a control group.

The wild-type *E. coli* XL1-Blue had significantly low glycerate dehydrogenase activity of 0.06 U/mg, but the recombinant strain transfected with a plasmid over-expressing glycerate dehydrogenase of *P. multocida* had glycerate dehydrogenase activity of 1.4 U/mg protein or more, which was 23 times higher than that of the wild-type *E. coli* strain.

In the case of using NADH as a cofactor, the enzyme activity of glycerate dehydrogenase of *P. multocida* was measured, but in the case of using NADPH as a cofactor, an enzyme reaction was not carried out, such that it may be appreciated that the glycerate dehydrogenase of *P. multocida* did not have an enzyme activity for NADPH.

TABLE 4

Activity of glycerate dehydrogenase of *P. multocida* Concentration

| Recombinant strain | A unit of acivity of glycerate dehydrogenase * (U/mg of protein) | | Polymer composition (mol %) | | Polymer concentration |
|---|---|---|---|---|---|
| | 10 h | 70 h | LA | GA | (weigh %) |
| XL1-Blue/pBluescript + pTac15k | 0.06 | 0.03 | — | — | — |
| XL1-Blue/pPs619C1437-CpPCT540 + pTac15kPmu0559 | 1.60 | 1.40 | 49 | 51 | 13.5 |

In producing the polymer containing lactate in the recombinant strain, since a step of producing lactyl-CoA is a rate-limiting step deteriorating polymer production efficiency, in order to increase the content of the lactate in the strain, a JLXF5 strain in which several metabolic pathways competitively using the lactate precursor were deleted in the chromosome of *E. coli* XL1-Blue was constructed. In addition, a lacIq gene under a control of a trc promoter was also deleted (See Table 1 and FIGS. 1 to 4).

As shown in Table 5, the *E. coli* JLXF5 strain expressing Pct540, PhaC1437, and glycerate dehydrogenase of *P. multocida* produced P(57.2 mol % LA-co-42.8 mol % GA) at a polymer concentration of 20.3 weight % or more without IPTG induction.

When the concentration of the lactate in the strain was increase, the lactate fraction in PLGA was increased. In the case of adding IPTG, the polymer concentration was increased from 20.3 to 26.9 weight %, and a composition of the monomer was barely changed.

TABLE 5

Composition and concentration of PLAG copolymer produced in recombinant *E. coli* Polymer concentration

| Recombinant strain | polymer | Polymer composition (mol %) | | Polymer concentration (wt %) |
|---|---|---|---|---|
| | | LA | GA | |
| XB/pPs619C1437-CpPCT540 + pTac15kPmu0559[1] | P(LA-co-GA) | 47.8 | 52.2 | 12.3 |
| JLXF5/pPs619C1437-CpPCT540 + pTac15kPmu0559[1] | P(LA-co-GA) | 54.6 | 45.4 | 26.9 |
| JLXF5/pPs619C1437-CpPCT540 + pTac15kPmu0559 | P(LA-co-GA) | 57.2 | 42.8 | 20.3 |
| JLXF6/pPs619C1437-CpPCT540 + pTac15kPmu0559 | P(LA-co-GA) | 43.7 | 56.2 | 23.9 |
| JLXF7/pPs619C1437-CpPCT540 + pTac15kPmu0559 | P(LA-co-GA) | 40.2 | 59.8 | 29.6 |
| JLXF8/pPs619C1437-CpPCT540 + pTac15kPmu0559 | P(LA-co-GA) | 38.4 | 61.6 | 32.6 |

In order to express ldhA and acs genes of chromosome under a control of a [1]trc promoter and genes of glycerate dehydrogenase of *P. multocida* under a control of a tac promoter of the plasmid, when a concentration of the culturing solution was 0.5 of OD600, 1 mM IPTG was treated.

Example 3

Production of PLGA Having High Glycolate Content Through Metabolic Engineering of *E. coli*

The PLGA was successfully produced from glucose using the recombinant XL1-Blue strains and recombinant JLXF5 strains in Example 2, but a concentration of the produced polymer was low. In order to improve PLGA biosynthesis in the recombinant strains, a glycolate synthesis pathway was enhanced in the JLXF5 strain modulated so as to efficiently produce lactate from glucose. In addition, an increase in the glycolate content may be advantageous for allowing glycolyl-CoA to start synthesis of the polymer. In order to increase synthesis of glycolate, the aceB and iclR genes involved in glyoxylate shunt were deleted, and the aceA gene was amplified.

In order to increase a glyoxylate pathway, a one-step inactivation method (Datsenko and Wanner, 2000) of deleting the iclR (isocitrate lyase regulator) and aceB (malate synthase) gene in the chromosome DNA and replacing the promoter of aceA (isocitrate lyase) gene with the trc promoter was used.

When the iclR gene was deleted, the concentration of PLGA produced in the recombinant strain was increased from 14.2 to 23.9 weight %, and the glycolate monomer fraction in the PLGA polymer was increased from 42.8 mol % to 56.2 mol %. In the case of additionally deleting the aceB gene and amplifying aceA gene, the concentration of PLGA produced in the recombinant strain was 32.6 weight %, which was 2.3 times higher than that of PLGA produced in JLFX5 strain. Further, the glycolate monomer was increased to 61.6 mol % or more.

Example 4

Characteristics of PLGA Synthesized in Recombinant *E. coli*

A monomer component of the copolymer synthesized in the present invention was analyzed using a gas chromatography, and the polymer was purified from cells by an organic solvent extraction method (Jacque et al., Biochem. Eng J 39:15-27, 2008). A molecular weight of the polymer was measured using nuclear magnetic resonance (NMR) spectroscopy and gel permeation chromatography (GPC).

Figure 5:
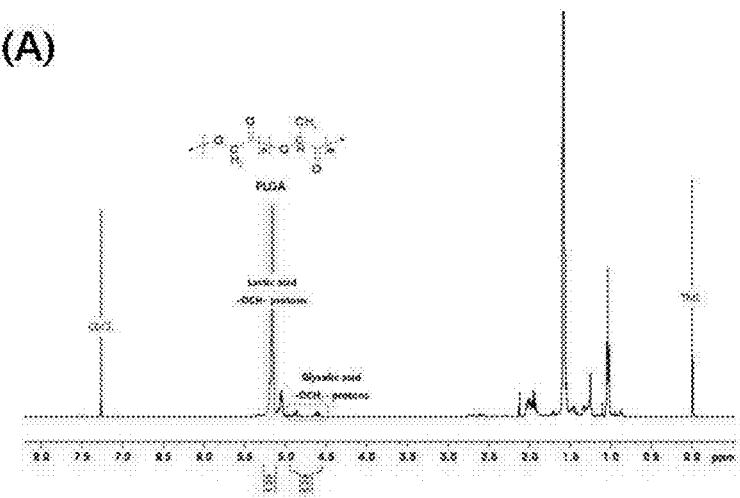
FIG. 5A-C show NMR results of PLGA which is produced by recombinant E. coli constructed in the present invention.
Figure 5:
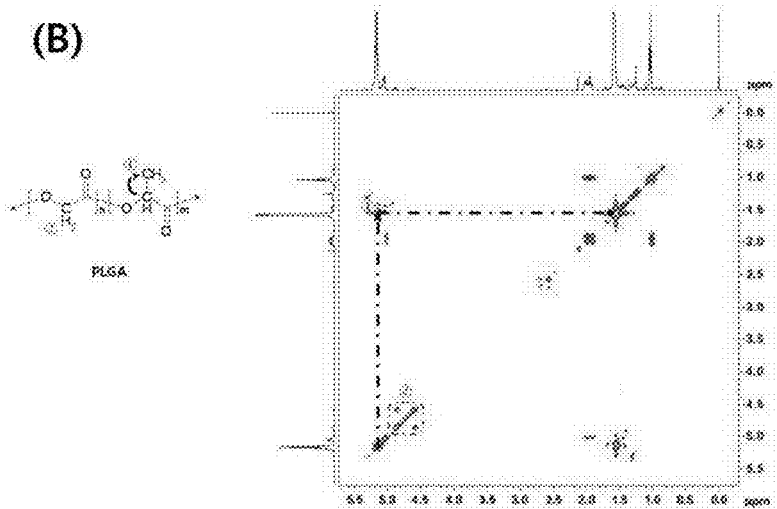
Figure 5:
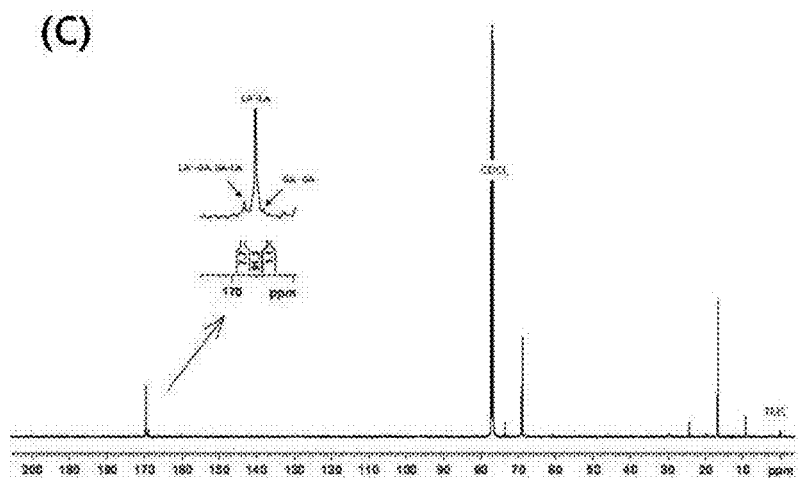

The PLGA produced by the *E. coli* JLXF5 had the same structure as that of chemically synthesized PLGA (See FIG. 1A). In a 500 MHz $^1$H NMR spectrum of the PLGA, an oxymethine proton (—OCH—) of LA was shown at 5.2 ppm and a methyl proton (—CH$_3$) of GA was shown at 4.6 to 4.9 ppm (FIG. 5A).

Internal 3-bond coupling of protons was confirmed in 1H-1H COSY spectrum, and the structure of PLGA became clear therefrom. Coupling between the oxymethine proton of LA and a methylene proton adjacent thereto was confirmed as a cross peak at 5.1 ppm/1.6 ppm (FIG. 5B). Coupling between methylene protons of GA was confirmed as a cross peak present at 4.6 to 4.9 ppm. In a 125 MHz $^{13}$C NMR spectrum of PLGA, a carbonyl carbon peak of GA*-GA sequence was shown at 169.4 ppm, a carbonyl peak of LA*-LA and LA-LA* sequences was shown at 169.63 ppm, and a carbonyl peak of LA*-GA+GA-LA* sequences was shown at 169.80 ppm (FIG. 5C).

INDUSTRIAL APPLICABILITY

As set forth above, according to the present invention, the poly(lactate-co-glycolate) in which the concentration of the glycolate fraction is high may be prepared at a high concentration without supplying exogenous glyoxylate.

Although the present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

---

The invention claimed is:

1. A recombinant microorganism having producibility of poly(lactate-co-glycolate), wherein the microorganism is transfected so that a gene coding poly(hydroxyalkanoate) (PHA) synthase, a gene coding propionyl-CoA transferase, and a gene coding glycerate dehydrogenase (EC 1.1.1.26) are inserted.

2. The recombinant microorganism of claim 1, wherein the propionate CoA-transferase is propionate CoA-transferase of *C. propionicum* or Pct540, which is a mutant enzyme of propionate CoA-transferase of *C. propionicum*.

3. The recombinant microorganism of claim 1, wherein the poly(hydroxyalkanoate) (PHA) synthase is PHA synthase of *Pseudomonas* sp. 6-19 or a mutant enzyme of PHA synthase of *Pseudomonas* sp. 6-19.

4. The recombinant microorganism of claim 3, wherein the gene coding the mutant enzyme of the PHA synthase has a base sequence corresponding to an amino acid sequence including at least one mutation selected from a group consisting of E130D, S325T, L412M, S477R, S477H, S477F, S477Y, S477G, Q481M, Q481K, and Q481R in an amino acid sequence of SEQ ID No: 1.

5. The recombinant microorganism of claim 3, wherein the gene coding the mutant enzyme of the PHA synthase has a base sequence corresponding to an amino acid sequence selected from a group consisting of:
   an amino acid sequence (C1335) in which E130D, S325T, L412M, S477G, and Q481M in the amino acid sequence of SEQ ID No: 1 are mutated;
   an amino acid sequence (C1310) in which E130D, S477F, and Q481K in the amino acid sequence of SEQ ID No: 1 are mutated; and
   an amino acid sequence (C1312) in which E130D, S477F, and Q481R in the amino acid sequence of SEQ ID No: 1 are mutated.

6. The recombinant microorganism of claim 1, wherein the gene coding glycerate dehydrogenase (EC 1.1.1.26) is derived from *Pasteurella multocida*.

7. The recombinant microorganism of claim 6, wherein the gene coding glycerate dehydrogenase has a base sequence of SEQ ID No: 2.

8. A recombinant microorganism having producibility of poly(lactate-co-glycolate), wherein the microorganism is transfected so that a gene coding PHA synthase, a gene coding propionyl-CoA transferase, and a gene coding glycerate dehydrogenase (EC 1.1.1.26) are inserted, and a gene (iclR) coding isocitrate lyase regulator or aceB (malate synthase) gene is deleted.

9. The recombinant microorganism of claim 8, wherein the propionate CoA-transferase is propionate CoA-transferase of *C. propionicum* or Pct540, which is a mutant enzyme of propionate CoA-transferase of *C. propionicum*.

10. The recombinant microorganism of claim 8, wherein the poly(hydroxyalkanoate) (PHA) synthase is PHA synthase of *Pseudomonas* sp. 6-19 or a mutant enzyme of PHA synthase of *Pseudomonas* sp. 6-19.

11. The recombinant microorganism of claim 10, wherein the gene coding the mutant enzyme of the PHA synthase has a base sequence corresponding to an amino acid sequence including at least one mutation selected from a group consisting of E130D, S325T, L412M, S477R, S477H, S477F, S477Y, S477G, Q481M, Q481K, and Q481R in an amino acid sequence of SEQ ID No: 1.

12. The recombinant microorganism of claim 10, wherein the gene coding the mutant enzyme of the PHA synthase has a base sequence corresponding to an amino acid sequence selected from a group consisting of:
   an amino acid sequence (C1335) in which E130D, S325T, L412M, S477G, and Q481M in the amino acid sequence of SEQ ID No: 1 are mutated;
   an amino acid sequence (C1310) in which E130D, S477F, and Q481K in the amino acid sequence of SEQ ID No: 1 are mutated; and
   an amino acid sequence (C1312) in which E130D, S477F, and Q481R in the amino acid sequence of SEQ ID No: 1 are mutated.

13. The recombinant microorganism of claim 10, wherein the gene coding glycerate dehydrogenase (EC 1.1.1.26) is derived from *Pasteurella multocida* or *E. coli*.

14. The recombinant microorganism of claim 13, wherein the gene coding glycerate dehydrogenase has a base sequence of SEQ ID No: 2.

15. The recombinant microorganism of claim 10, wherein both of the gene (iclR) coding isocitrate lyase regulator and a gene (aceB) coding isocitrate lyase are deleted.

16. The recombinant microorganism of claim 10, wherein the gene (aceA) coding isocitrate lyase is additionally amplified.

17. A method of preparing poly(lactate-co-glycolate) (PLGA) including: culturing the recombinant microorganism of claim 1 to produce poly(lactate-co-glycolate); and obtaining the produced PLGA.

18. A method of preparing poly(lactate-co-glycolate) (PLGA) including: culturing the recombinant microorganism of claim 10 to produce poly(lactate-co-glycolate); and obtaining the produced PLGA.

* * * * *

UNITED STATES PATENT AND TRADEMARK OFFICE
CERTIFICATE OF CORRECTION

Page 1 of 1

PATENT NO. : 8,883,463 B2
APPLICATION NO. : 14/004437
DATED : November 11, 2014
INVENTOR(S) : Sang Yup Lee It is certified that error appears in the above-identified patent and that said Letters Patent is hereby corrected as shown below:

In The Specification

Column 5, line 21: "and 0.02 of" should be -- and 0.02 g of --.

Signed and Sealed this
Thirtieth Day of December, 2014

Michelle K. Lee
*Deputy Director of the United States Patent and Trademark Office*

SEQUENCE LISTING

```
<160> NUMBER OF SEQ ID NOS: 51

<210> SEQ ID NO 1
<211> LENGTH: 559
<212> TYPE: PRT
<213> ORGANISM: Pseudomonas sp. 6-19

<400> SEQUENCE: 1

Met Ser Asn Lys Ser Asn Asp Glu Leu Lys Tyr Gln Ala Ser Glu Asn
1               5                   10                  15

Thr Leu Gly Leu Asn Pro Val Val Gly Leu Arg Gly Lys Asp Leu Leu
            20                  25                  30

Ala Ser Ala Arg Met Val Leu Arg Gln Ala Ile Lys Gln Pro Val His
        35                  40                  45

Ser Val Lys His Val Ala His Phe Gly Leu Glu Leu Lys Asn Val Leu
    50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240
```

```
Arg Phe Cys Leu Arg Asn Asn Val Gln Thr Phe Ile Val Ser Trp Arg
                245                 250                 255
Asn Pro Thr Lys Glu Gln Arg Glu Trp Gly Leu Ser Tyr Ile Glu
            260                 265                 270
Ala Leu Lys Glu Ala Val Asp Val Val Thr Ala Ile Thr Gly Ser Lys
            275                 280                 285
Asp Val Asn Met Leu Gly Ala Cys Ser Gly Gly Ile Thr Cys Thr Ala
        290                 295                 300
Leu Leu Gly His Tyr Ala Ala Ile Gly Glu Asn Lys Val Asn Ala Leu
305                 310                 315                 320
Thr Leu Leu Val Ser Val Leu Asp Thr Thr Leu Asp Ser Asp Val Ala
                325                 330                 335
Leu Phe Val Asn Glu Gln Thr Leu Glu Ala Ala Lys Arg His Ser Tyr
            340                 345                 350
Gln Ala Gly Val Leu Glu Gly Arg Asp Met Ala Lys Val Phe Ala Trp
            355                 360                 365
Met Arg Pro Asn Asp Leu Ile Trp Asn Tyr Trp Val Asn Asn Tyr Leu
        370                 375                 380
Leu Gly Asn Glu Pro Pro Val Phe Asp Ile Leu Phe Trp Asn Asn Asp
385                 390                 395                 400
Thr Thr Arg Leu Pro Ala Ala Phe His Gly Asp Leu Ile Glu Leu Phe
                405                 410                 415
Lys Asn Asn Pro Leu Ile Arg Pro Asn Ala Leu Glu Val Cys Gly Thr
            420                 425                 430
Pro Ile Asp Leu Lys Gln Val Thr Ala Asp Ile Phe Ser Leu Ala Gly
        435                 440                 445
Thr Asn Asp His Ile Thr Pro Trp Lys Ser Cys Tyr Lys Ser Ala Gln
450                 455                 460
Leu Phe Gly Gly Asn Val Glu Phe Val Leu Ser Ser Ser Gly His Ile
465                 470                 475                 480
Gln Ser Ile Leu Asn Pro Pro Gly Asn Pro Lys Ser Arg Tyr Met Thr
                485                 490                 495
Ser Thr Glu Val Ala Glu Asn Ala Asp Glu Trp Gln Ala Asn Ala Thr
            500                 505                 510
Lys His Thr Asp Ser Trp Trp Leu His Trp Gln Ala Trp Gln Ala Gln
        515                 520                 525
Arg Ser Gly Glu Leu Lys Lys Ser Pro Thr Lys Leu Gly Ser Lys Ala
        530                 535                 540
Tyr Pro Ala Gly Glu Ala Ala Pro Gly Thr Tyr Val His Glu Arg
545                 550                 555

<210> SEQ ID NO 2
<211> LENGTH: 951
<212> TYPE: DNA
<213> ORGANISM: Pyrococcus multocida

<400> SEQUENCE: 2
atgttaaaaa ttgtttttct agatagtacc gcgatacctaa acatatccc gattcctcgc    60 ccaagttttc cacatcaatg ggttgaatat gagcatacga caccagatca agtcgtagaa   120
cgtatgcaag atgtagacat tgcggtaacc agtaaagtcc tctttagtcg tgaagtgatg   180
caacaattac ctaaattaaa attaatcgcg attacggcaa cagggaccaa taatgtggat   240
ttggtggctg cacaagaact tggaatcacg gtgaaaaatg tgacagggta ttcatctaca   300
accgtaccag aacatgtgat aggtctgata tatgcgctca acacagtat tatgagctgg   360
```

```
tatcgcgatc aattatctgc aaaatgggca gattgcaaac aatttttgtta ctttgattat    420 ccgattacag atgtgaaagg ctcaacccct ggtgtcgtgg gacgaggctg tttaggctct    480
gaaatcggtc gattagcgac cgcacttggc atgaatgtac tttatgcaga acataaaggt    540
gcgaaaacat gtcgtgaggg ttataccccct tttgaagacg tgttagcaca agcggatatc    600
ttgacattac attgcccatt gacggacacc acacaaaatc tgatcaatca agacacgtta    660
gctttgatga aaaaggcgc attttttaatt aatacagggc gtggtccttt agtggatgaa    720
caggcgttag tcgctgcatt agaaagtgga catcttggtg gtgccgcggt tgatgtgtta    780
gtgaaagaac cgcctgaaaa aaacaactca attatccaag ctgccacacg tttgcctaat    840
ttaattgtta ccccgcatat tgcttgggca tctgacagtg cggttaccac cttagtgaat    900
aaggtgaaac aaaacattga agactttgta aaaaatgagc agattgctta a           951
```

<210> SEQ ID NO 3  
<211> LENGTH: 39  
<212> TYPE: DNA  
<213> ORGANISM: Artificial  
<220> FEATURE:  
<223> OTHER INFORMATION: primer
<400> SEQUENCE: 3

```
gtagaattca tgttaaaaat tgttttttcta gatagtacc                          39
```

<210> SEQ ID NO 4  
<211> LENGTH: 38  
<212> TYPE: DNA  
<213> ORGANISM: Artificial  
<220> FEATURE:  
<223> OTHER INFORMATION: primer
<400> SEQUENCE: 4

```
gtatgcaact gcagttaagc aatctgctca ttttttac                            38
```

<210> SEQ ID NO 5  
<211> LENGTH: 71  
<212> TYPE: DNA  
<213> ORGANISM: Artificial  
<220> FEATURE:  
<223> OTHER INFORMATION: primer
<400> SEQUENCE: 5

```
tcgagcagat gatttactaa aaaagtttaa cattatcagg agagcattat taggtgacac    60
tatagaacgc g                                                         71
```

<210> SEQ ID NO 6  
<211> LENGTH: 70  
<212> TYPE: DNA  
<213> ORGANISM: Artificial  
<220> FEATURE:  
<223> OTHER INFORMATION: primer
<400> SEQUENCE: 6

```
gattttcata ggttaagcaa atcatcaccg cactgactat actctcgtat tcgagcagat    60
gatttactaa                                                           70
```

<210> SEQ ID NO 7  
<211> LENGTH: 70  
<212> TYPE: DNA  
<213> ORGANISM: Artificial  
<220> FEATURE:

<223> OTHER INFORMATION: primer

<400> SEQUENCE: 7
tgatcggcat tgcccagaag gggccgttta tgttgccaga cagcgctact tagtggatct    60
gatgggtacc    70

<210> SEQ ID NO 8
<211> LENGTH: 70
<212> TYPE: DNA
<213> ORGANISM: Artificial
<220> FEATURE:
<223> OTHER INFORMATION: primer

<400> SEQUENCE: 8
ggaagccgtt atagtgcctc agtttaagga tcggtcaact aatccttaac tgatcggcat    60
tgcccagaag    70

<210> SEQ ID NO 9
<211> LENGTH: 60
<212> TYPE: DNA
<213> ORGANISM: Artificial
<220> FEATURE:
<223> OTHER INFORMATION: primer

<400> SEQUENCE: 9
tcacgacagt aaccgcacct acactgtcat gacattgctc gccctatgt gtaacaaata    60

<210> SEQ ID NO 10
<211> LENGTH: 77
<212> TYPE: DNA
<213> ORGANISM: Artificial
<220> FEATURE:
<223> OTHER INFORMATION: primer

<400> SEQUENCE: 10
tgttatccgc tcacaattcc acacattata cgagccggat gattaattgt caacagctag    60
tggatctgat gggtacc    77

<210> SEQ ID NO 11
<211> LENGTH: 60
<212> TYPE: DNA
<213> ORGANISM: Artificial
<220> FEATURE:
<223> OTHER INFORMATION: primer

<400> SEQUENCE: 11
tcacgacagt aaccgcacct acactgtcat gacattgctc gccctatgt gtaacaaata    60

<210> SEQ ID NO 12
<211> LENGTH: 81
<212> TYPE: DNA
<213> ORGANISM: Artificial
<220> FEATURE:
<223> OTHER INFORMATION: primer

<400> SEQUENCE: 12
cgatgttggc aggaatggtg tgtttgtgaa tttggctcat ggtctgtttc ctgtgtgaaa    60
ttgttatccg ctcacaattc c    81

<210> SEQ ID NO 13
<211> LENGTH: 60
<212> TYPE: DNA
<213> ORGANISM: Artificial

-continued

<220> FEATURE:
<223> OTHER INFORMATION: primer

<400> SEQUENCE: 13
cgaattgcgc cattgttgca atggcggttt ttattgtttt tcacgacagt aaccgcacct    60

<210> SEQ ID NO 14
<211> LENGTH: 70
<212> TYPE: DNA
<213> ORGANISM: Artificial
<220> FEATURE:
<223> OTHER INFORMATION: primer

<400> SEQUENCE: 14
ttgttgatac atcgcctcgt actgctgagg gtttatcagg caacggtctg cgatgttggc    60
aggaatggtg                                                          70

<210> SEQ ID NO 15
<211> LENGTH: 71
<212> TYPE: DNA
<213> ORGANISM: Artificial
<220> FEATURE:
<223> OTHER INFORMATION: primer

<400> SEQUENCE: 15
ttacgggcct ataagccagg cgagatatga tctatatcaa tttctcatct taggtgacac    60
tatagaacgc g                                                        71

<210> SEQ ID NO 16
<211> LENGTH: 70
<212> TYPE: DNA
<213> ORGANISM: Artificial
<220> FEATURE:
<223> OTHER INFORMATION: primer

<400> SEQUENCE: 16
ttctttagtc agcgagttga aacgtactgc gtagccagat acacggatgg tagtggatct    60
gatgggtacc                                                          70

<210> SEQ ID NO 17
<211> LENGTH: 70
<212> TYPE: DNA
<213> ORGANISM: Artificial
<220> FEATURE:
<223> OTHER INFORMATION: primer

<400> SEQUENCE: 17
tatttggata atcaaatatt tactccgtat ttgcataaaa accatgcgag ttacgggcct    60
ataagccagg                                                          70

<210> SEQ ID NO 18
<211> LENGTH: 69
<212> TYPE: DNA
<213> ORGANISM: Artificial
<220> FEATURE:
<223> OTHER INFORMATION: primer

<400> SEQUENCE: 18
tctaattaca tagattgagt gaaggtacga gtaataacgt cctgctgctg ttctttagtc    60
agcgagttg                                                           69

<210> SEQ ID NO 19

```
<211> LENGTH: 71
<212> TYPE: DNA
<213> ORGANISM: Artificial
<220> FEATURE:
<223> OTHER INFORMATION: primer

<400> SEQUENCE: 19
attacgtgct gcaattgctg ccgcgcaggc aaatccgaat gcaaaaatcg taggtgacac    60
tatagaacgc g                                                         71

<210> SEQ ID NO 20
<211> LENGTH: 70
<212> TYPE: DNA
<213> ORGANISM: Artificial
<220> FEATURE:
<223> OTHER INFORMATION: primer

<400> SEQUENCE: 20
gaccgtagaa aacccatttg cccgcaggta cgtggatttt cagatcgtgc tagtggatct    60
gatgggtacc                                                           70

<210> SEQ ID NO 21
<211> LENGTH: 70
<212> TYPE: DNA
<213> ORGANISM: Artificial
<220> FEATURE:
<223> OTHER INFORMATION: primer

<400> SEQUENCE: 21
gtgcaaacct ttcaagccga tcttgccatt gtaggcgccg gtggcgcggg attacgtgct    60
gcaattgctg                                                           70

<210> SEQ ID NO 22
<211> LENGTH: 70
<212> TYPE: DNA
<213> ORGANISM: Artificial
<220> FEATURE:
<223> OTHER INFORMATION: primer

<400> SEQUENCE: 22
ttagattgta acgacaccaa tcagcgtgac aactgtcagg atagcagcca gaccgtagaa    60
aacccatttg                                                           70

<210> SEQ ID NO 23
<211> LENGTH: 71
<212> TYPE: DNA
<213> ORGANISM: Artificial
<220> FEATURE:
<223> OTHER INFORMATION: primer

<400> SEQUENCE: 23
tcgagcagat gatttactaa aaaagtttaa cattatcagg agagcattat taggtgacac    60
tatagaacgc g                                                         71

<210> SEQ ID NO 24
<211> LENGTH: 70
<212> TYPE: DNA
<213> ORGANISM: Artificial
<220> FEATURE:
<223> OTHER INFORMATION: primer

<400> SEQUENCE: 24
tgatcggcat tgcccagaag gggccgttta tgttgccaga cagcgctact tagtggatct    60
```

-continued gatgggtacc                                                          70

<210> SEQ ID NO 25
<211> LENGTH: 70
<212> TYPE: DNA
<213> ORGANISM: Artificial
<220> FEATURE:
<223> OTHER INFORMATION: primer

<400> SEQUENCE: 25
gattttcata ggttaagcaa atcatcaccg cactgactat actctcgtat tcgagcagat    60
gatttactaa                                                          70

<210> SEQ ID NO 26
<211> LENGTH: 70
<212> TYPE: DNA
<213> ORGANISM: Artificial
<220> FEATURE:
<223> OTHER INFORMATION: primer

<400> SEQUENCE: 26
ggaagccgtt atagtgcctc agtttaagga tcggtcaact aatccttaac tgatcggcat    60
tgcccagaag                                                          70

<210> SEQ ID NO 27
<211> LENGTH: 71
<212> TYPE: DNA
<213> ORGANISM: Artificial
<220> FEATURE:
<223> OTHER INFORMATION: primer

<400> SEQUENCE: 27
tcagaccgtt tcccgcgtgg tgaaccaggc cagccacgtt tctgcgaaaa taggtgacac    60
tatagaacgc g                                                        71

<210> SEQ ID NO 28
<211> LENGTH: 70
<212> TYPE: DNA
<213> ORGANISM: Artificial
<220> FEATURE:
<223> OTHER INFORMATION: primer

<400> SEQUENCE: 28
tgccagctgc attaatgaat cggccaacgc gcggggagag gcggtttgcg tagtggatct    60
gatgggtacc                                                          70

<210> SEQ ID NO 29
<211> LENGTH: 70
<212> TYPE: DNA
<213> ORGANISM: Artificial
<220> FEATURE:
<223> OTHER INFORMATION: primer

<400> SEQUENCE: 29
gtgaaaccag taacgttata cgatgtcgca gagtatgccg gtgtctctta tcagaccgtt    60
tcccgcgtgg                                                          70

<210> SEQ ID NO 30
<211> LENGTH: 70
<212> TYPE: DNA
<213> ORGANISM: Artificial
<220> FEATURE:

<223> OTHER INFORMATION: primer

<400> SEQUENCE: 30
cattaattgc gttgcgctca ctgcccgctt tccagtcggg aaacctgtcg tgccagctgc    60
attaatgaat                                                          70

<210> SEQ ID NO 31
<211> LENGTH: 60
<212> TYPE: DNA
<213> ORGANISM: Artificial
<220> FEATURE:
<223> OTHER INFORMATION: primer

<400> SEQUENCE: 31
catctaatgc aatacgtgtc ccgagcggta gccagatgct aggtgacact atagaacgcg    60

<210> SEQ ID NO 32
<211> LENGTH: 77
<212> TYPE: DNA
<213> ORGANISM: Artificial
<220> FEATURE:
<223> OTHER INFORMATION: primer

<400> SEQUENCE: 32
tgttatccgc tcacaattcc acacattata cgagccggat gattaattgt caacagctag    60
tggatctgat gggtacc                                                  77

<210> SEQ ID NO 33
<211> LENGTH: 62
<212> TYPE: DNA
<213> ORGANISM: Artificial
<220> FEATURE:
<223> OTHER INFORMATION: primer

<400> SEQUENCE: 33
gatcgggaat gattaaacct ttacgcgtaa tgcgtgggct ttcatctaat gcaatacgtg    60
tc                                                                  62

<210> SEQ ID NO 34
<211> LENGTH: 81
<212> TYPE: DNA
<213> ORGANISM: Artificial
<220> FEATURE:
<223> OTHER INFORMATION: primer

<400> SEQUENCE: 34
tcttgtcgta ctgttttgtg ctataaacgg cgagtttcat ggtctgtttc ctgtgtgaaa    60
ttgttatccg ctcacaattc c                                             81

<210> SEQ ID NO 35
<211> LENGTH: 60
<212> TYPE: DNA
<213> ORGANISM: Artificial
<220> FEATURE:
<223> OTHER INFORMATION: primer

<400> SEQUENCE: 35
ggtgatatgc gcaagctgac aatctcccac cagataacgg agatcgggaa tgattaaacc    60

<210> SEQ ID NO 36
<211> LENGTH: 71
<212> TYPE: DNA
<213> ORGANISM: Artificial

<220> FEATURE:
<223> OTHER INFORMATION: primer

<400> SEQUENCE: 36
caaaaaattc cagctcaaag ccaaaggact cgttcacctg ttgcaggtac ttcttgtcgt    60
actgttttgt g                                                        71

<210> SEQ ID NO 37
<211> LENGTH: 60
<212> TYPE: DNA
<213> ORGANISM: Artificial
<220> FEATURE:
<223> OTHER INFORMATION: primer

<400> SEQUENCE: 37
tcacgacagt aaccgcacct acactgtcat gacattgctc gccctatgt gtaacaaata    60

<210> SEQ ID NO 38
<211> LENGTH: 77
<212> TYPE: DNA
<213> ORGANISM: Artificial
<220> FEATURE:
<223> OTHER INFORMATION: primer

<400> SEQUENCE: 38
tgttatccgc tcacaattcc acacattata cgagccggat gattaattgt caacagctag    60
tggatctgat gggtacc                                                   77

<210> SEQ ID NO 39
<211> LENGTH: 60
<212> TYPE: DNA
<213> ORGANISM: Artificial
<220> FEATURE:
<223> OTHER INFORMATION: primer

<400> SEQUENCE: 39
tcacgacagt aaccgcacct acactgtcat gacattgctc gccctatgt gtaacaaata    60

<210> SEQ ID NO 40
<211> LENGTH: 81
<212> TYPE: DNA
<213> ORGANISM: Artificial
<220> FEATURE:
<223> OTHER INFORMATION: primer

<400> SEQUENCE: 40
cgatgttggc aggaatggtg tgtttgtgaa tttggctcat ggtctgtttc ctgtgtgaaa    60
ttgttatccg ctcacaattc c                                              81

<210> SEQ ID NO 41
<211> LENGTH: 60
<212> TYPE: DNA
<213> ORGANISM: Artificial
<220> FEATURE:
<223> OTHER INFORMATION: primer

<400> SEQUENCE: 41
cgaattgcgc cattgttgca atggcggttt ttattgtttt tcacgacagt aaccgcacct    60

<210> SEQ ID NO 42
<211> LENGTH: 70
<212> TYPE: DNA
<213> ORGANISM: Artificial
<220> FEATURE:

<223> OTHER INFORMATION: primer

<400> SEQUENCE: 42
ttgttgatac atcgcctcgt actgctgagg gtttatcagg caacggtctg cgatgttggc    60
aggaatggtg    70

<210> SEQ ID NO 43
<211> LENGTH: 80
<212> TYPE: DNA
<213> ORGANISM: Artificial
<220> FEATURE:
<223> OTHER INFORMATION: primer

<400> SEQUENCE: 43
tgaaaatgat ttccacgata cagaaaaaag agactgtcat ggtcgcaccc attccgcatc    60
agagcagatt gtactgagag    80

<210> SEQ ID NO 44
<211> LENGTH: 81
<212> TYPE: DNA
<213> ORGANISM: Artificial
<220> FEATURE:
<223> OTHER INFORMATION: primer

<400> SEQUENCE: 44
tgatgggcag aatattgcct ctgcccgcca gaaaaagtca gcgcattcca ccgtacctga    60
ttctgtggat aaccgtatta c    81

<210> SEQ ID NO 45
<211> LENGTH: 70
<212> TYPE: DNA
<213> ORGANISM: Artificial
<220> FEATURE:
<223> OTHER INFORMATION: primer

<400> SEQUENCE: 45
gcggataaat cgctggaagc caataacggt cacgatggca catggatcgc cgcgtcatac    60
acatacgatt    70

<210> SEQ ID NO 46
<211> LENGTH: 70
<212> TYPE: DNA
<213> ORGANISM: Artificial
<220> FEATURE:
<223> OTHER INFORMATION: primer

<400> SEQUENCE: 46
ggttgagtcc actctttctg taattcttca atttgttgtg tacgggtttt catggtctgt    60
ttcctgtgtg    70

<210> SEQ ID NO 47
<211> LENGTH: 27
<212> TYPE: DNA
<213> ORGANISM: Artificial
<220> FEATURE:
<223> OTHER INFORMATION: primer

<400> SEQUENCE: 47
gaattcatgg atatcatctt ttatcac    27

<210> SEQ ID NO 48
<211> LENGTH: 27

```
<212> TYPE: DNA
<213> ORGANISM: Artificial
<220> FEATURE:
<223> OTHER INFORMATION: primer

<400> SEQUENCE: 48
ggtaccttag tagccgcgtg cgcggtc                                          27

<210> SEQ ID NO 49
<211> LENGTH: 26
<212> TYPE: DNA
<213> ORGANISM: Artificial
<220> FEATURE:
<223> OTHER INFORMATION: primer

<400> SEQUENCE: 49
gaattcatgc ccagcccgcg tcgcgc                                           26

<210> SEQ ID NO 50
<211> LENGTH: 26
<212> TYPE: DNA
<213> ORGANISM: Artificial
<220> FEATURE:
<223> OTHER INFORMATION: primer

<400> SEQUENCE: 50
ggtacctcag ctgaccacgc ggcgtg                                           26

<210> SEQ ID NO 51
<211> LENGTH: 939
<212> TYPE: DNA
<213> ORGANISM: Escherichia coli

<400> SEQUENCE: 51
atggatatca tcttttatca cccaacgttc gatacccaat ggtggattga ggcactgcgc      60
aaagctattc ctcaggcaag agtcagagca tggaaaagcg gagataatga ctctgctgat    120
tatgctttag tctggcatcc tcctgttgaa atgctggcag ggcgcgatct taaagcggtg    180
ttcgcactcg gggccggtgt tgattctatt ttgagcaagc tacaggcaca ccctgaaatg    240 ctgaacccttt ctgttccact ttttcgcctg gaagataccg gtatgggcga gcaaatgcag    300
gaatatgctg tcagtcaggt gctgcattgg tttcgacgtt ttgacgatta tcgcatccag    360
caaaatagtt cgcattggca accgctgcct gaatatcatc gggaagattt taccatcggc    420
attttgggcg caggcgtact gggcagtaaa gttgctcaga gtctgcaaac ctggcgcttt    480
ccgctgcgtt gctggagtcg aacccgtaaa tcgtggcctg gcgtgcaaag ctttgccgga    540
cgggaagaac tgtctgcatt tctgagccaa tgtcgggtat tgattaattt gttaccgaat    600 accctgaaa ccgtcggcat tattaatcaa caattactcg aaaaattacc ggatggcgcg    660
tatctcctca acctggcgcg tggtgttcat gttgtggaag atgacctgct cgcggcgctg    720
gatagcggca agttaaaggc gcaatgttg gatgtttta atcgtgaacc cttaccgcct    780
gaaagtccgc tctggcaaca tccacgcgtg acgataacac cacatgtcgc cgcgattacc    840
cgtcccgctg aagctgtgga gtacatttct cgcaccattg cccagctcga aaaggggag    900 agggtctgcg ggcaagtcga ccgcgcacgc ggctactaa                           939
```